US006277607B1

(12) United States Patent
Tyagi et al.

(10) Patent No.: US 6,277,607 B1
(45) Date of Patent: Aug. 21, 2001

(54) HIGH SPECIFICITY PRIMERS, AMPLIFICATION METHODS AND KITS

(76) Inventors: Sanjay Tyagi, 20 Waterside Plz., Apt. 16E, New York, NY (US) 10010; Fred R. Kramer, 561 W. 231st St., Riverdale, NY (US) 10463; Robert Vartikian, 809 W. 177th St., Apt. 6H, New York, NY (US) 10033

( * ) Notice: Subject to any disclaimer, the term of this patent is extended or adjusted under 35 U.S.C. 154(b) by 0 days.

(21) Appl. No.: 09/317,350

(22) Filed: May 24, 1999

(51) Int. Cl.$^7$ ............................ C12P 19/34; C12Q 1/68; G01N 33/00; C07H 21/02; C07H 21/04
(52) U.S. Cl. ...................... 435/91.2; 435/6; 435/91.1; 436/94; 536/23.1; 536/24.3; 536/24.33
(58) Field of Search .................. 435/6, 91.1, 91.2, 435/975, 183; 536/23.1, 24.3, 24.33, 25.3; 436/94, 501

(56) References Cited

U.S. PATENT DOCUMENTS

| 5,118,801 | 6/1992 | Lizardi et al. . | |
|---|---|---|---|
| 5,312,728 | 5/1994 | Lizardi et al. . | |
| 5,487,972 | 1/1996 | Gelfand et al. . | |
| 5,503,979 | 4/1996 | Kramer et al. . | |
| 5,538,848 | 7/1996 | Livak et al. . | |
| 5,866,336 | * 2/1999 | Nazarenko et al. | 435/6 |
| 5,925,517 | 7/1999 | Tyagi et al. . | |
| 6,037,130 | 3/2000 | Tyagi et al. . | |
| 6,090,552 | * 7/2000 | Nazarenko et al. | 435/6 |
| 6,117,635 | * 9/2000 | Nazarenko et al. | 435/6 |

FOREIGN PATENT DOCUMENTS

| WO97/39008 | 10/1997 | (EP) . |
|---|---|---|
| WO98/02449 | 1/1998 | (EP) . |

OTHER PUBLICATIONS

Giesendorf et al., Molecular beacons: a new approach for semiautomated mutation analysis. Clin. Chem. 44, 482–486, 1998.*

Blok et al., "Amplificable Hybridization Probes Containing a Molecular Switch", *Molecular and Cellular Probes*, 11:187–194, 1997.

Bonnet et a., "Thermodynamic Basis of the Enhanced Specificity of Structured DNA Probes", *Proc. Natl. Acad. Sci. USA*, 96:6171–6176, 1999.

Haas et al., "Primer Design for Large Scale Sequencing", *Nucleic Acids Research*, 26(12):3006–3012, 1998.

Kostrikis et al., "Spectral Genotyping of Human Alleles", *Science*, 279:1228–1229, 1998.

Kramer et al., "Replicatable RNA Reporters", *Nature*, 339 No. 6223: pp. 401–402, 1989.

Lengauer et al., "Genetic Instabilities in Human Cancers", *Nature*, 396:643–649, 1998.

Leone et al., "Molecular Beacon Probes Combined with Amplification by NASBA Enable Homogeneous, Real–Time Detection of RNA", *Nucl. Acids Res.*, 26, No. 9:2150–2155, 1998.

(List continued on next page.)

*Primary Examiner*—Ethan Whisenant
*Assistant Examiner*—Frank Lu
(74) *Attorney, Agent, or Firm*—Fish & Richardson P.C.

(57) ABSTRACT

For nucleic acid amplification including extension of primers by a DNA polymerase, high specificity primers are provided. The primers include a type of hairpin structure in which a single-stranded loop separates complementary 3' and 5' arms and in which the loop and the 3' arm are complementary to the target nucleic acid. Amplification methods, assays and kits including such primers are included in the invention.

16 Claims, 4 Drawing Sheets

OTHER PUBLICATIONS

Marras et al., "Multiplex Detection of Single–Nucleotide Variations Using Molecular Beacons", *Genetic Analysis: Biomolecular Engineering*, 14:151–156, 1999.

Monia et al., Selective Inhibition of Mutant Ha–ras mRNA Expression by Antisense Oligonucleotides:, *The Journal of Biological Chemistry*, 267(28): 19954–19962, 1992.

Moran et al., "Non–Hydrogen Bonding 'Terminator' Nucleosides Increase the 3'–End Homogeneity of Enzymatic RNA and DNA Synthesis", *Nucleic Acids Research*, 24:2044–2052, 1996.

Nazarenko et al., "A Closed Tube Format for Amplification and Detection of DNA Based on Energy Transfer", *Nucleic Acids Research*, 25(12):2516–2521, 1997.

Newton et al., "Analysis of any Point Mutation in DNA. The Amplification Refractory Mutation System (ARMS)", *Nucleic Acids Research*, 17(7):2503–2516, 1989.

Serra et al., "Predicting Thermodynamic Properties of RNA", *Methods in Enzymology*, 259:242–261, 1995.

Tyagi et al., "Extremely Sensitive, Background–Free Gene Detection Using Binary Probes and Qβ Replicase", *Proc. Nat. Acad. Sci. USA*, 93:5395–5400, 1996.

Tyagi et al., "Molecular Beacons: Probes that Fluoresce upon Hybridization", *Nature Biotechnology*, 14:303–308, 1996.

Tyagi et al., "Multicolor Molecular Beacons for Allele Discrimination", *Nature Biotechnology*, 16:49–53, 1998.

Vet et al., "Multiplex Detection of Four Pathogenic Retroviruses Using Molecular Beacons", *Proc. Natl. Acad. Sci. USA*, 96:6394–6399, 1999.

Whitcombe et al. "Detection of PCR Products Using Self–Probing Amplicons and Fluorescence", *Nature Biotechnology*, 17:804–807, 1999.

Wittwer et al., "Continuous Fluorescence Monitoring of Rapid Cycle DNA Amplification", *Biotechniques*, 22:130–138, 1997.

Wu et al., "Allele–specific Enzymatic Amplification of β–globin Genomic DNA for Diagnosis of Sickle Cell Anemia", *Proc. Natl. Acad. Sci. USA*, 86:2757–2760, 1989.

Zubritsky, "Pinning Down PCR", *Analytical Chemistry News & Features*, 71:191A–195A, 1999.

Giesendorf et al., Molecular Beacons: a new approach for semiautomatic mutation analysis. Clin. Chem. Mar. 1998, vol. 44, No. 3, pp. 482–486.

* cited by examiner

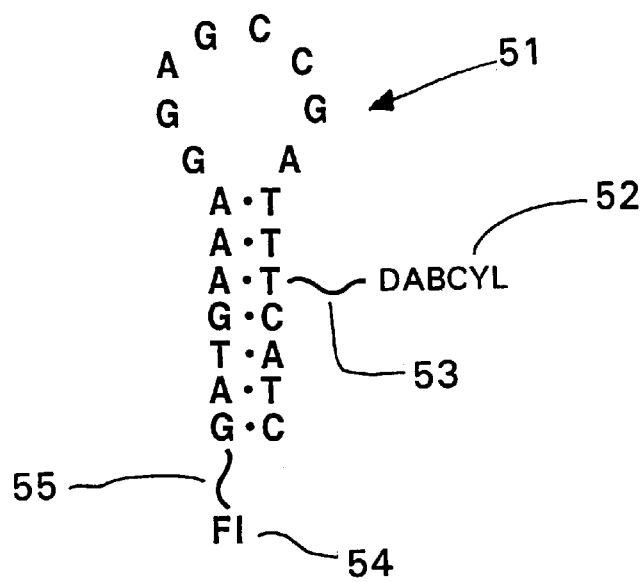
FIG. 5
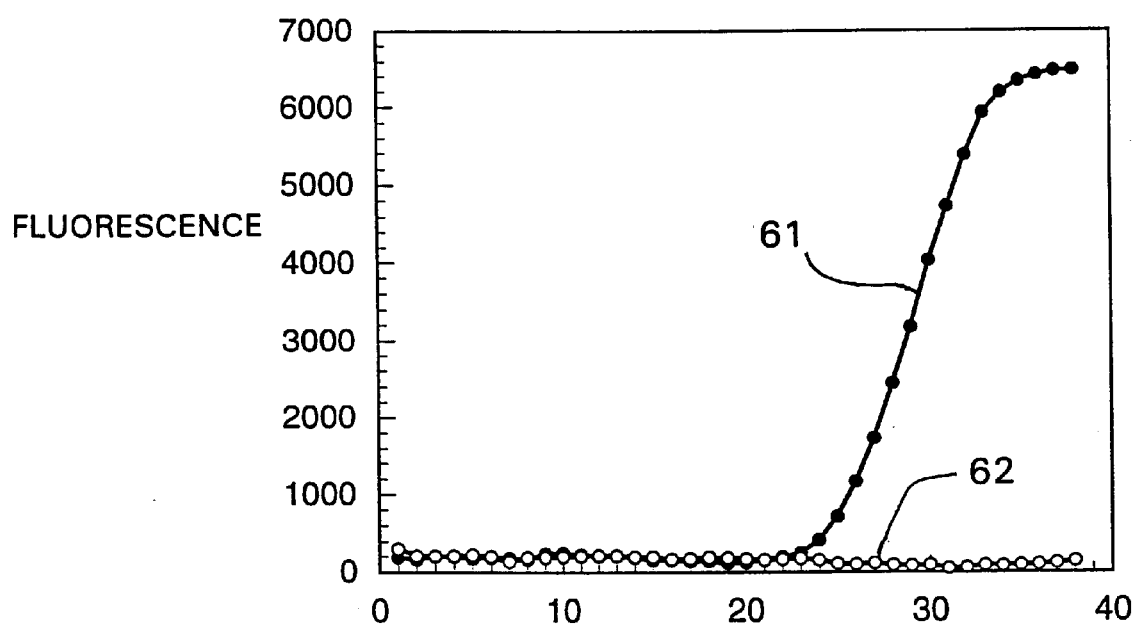
FIG. 6  CYCLE NUMBER

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: oligonucleotide for PCR

<400> SEQUENCE: 1
gatgaaagga gccgatttca tc                                              22

<210> SEQ ID NO 2
<211> LENGTH: 22
<212> TYPE: DNA
<213> ORGANISM: Artificial Sequence
<220> FEATURE:
<223> OTHER INFORMATION: oligonucleotide for PCR
```

-continued

```
<400> SEQUENCE: 2
gatgaaagga gtcgatttca tc                                              22

<210> SEQ ID NO 3
<211> LENGTH: 17
<212> TYPE: DNA
<213> ORGANISM: Artificial Sequence
<220> FEATURE:
<223> OTHER INFORMATION: oligonucleotide for PCR

<400> SEQUENCE: 3
ggccggtggt cgccgcg                                                    17

<210> SEQ ID NO 4
<211> LENGTH: 19
<212> TYPE: DNA
<213> ORGANISM: Artificial Sequence
<220> FEATURE:
<223> OTHER INFORMATION: oligonucleotide for PCR

<400> SEQUENCE: 4
acgtgacaga ccgccgggc                                                  19

<210> SEQ ID NO 5
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 5
cgcggccggt ggtcgccgcg                                                 20

<210> SEQ ID NO 6
<211> LENGTH: 25
<212> TYPE: DNA
<213> ORGANISM: Artificial Sequence
<220> FEATURE:
<223> OTHER INFORMATION: oligonucleotide for PCR

<400> SEQUENCE: 6
gcccggacgt gacagaccgc cgggc                                           25
```

HIGH SPECIFICITY PRIMERS, AMPLIFICATION METHODS AND KITS

This invention relates to nucleic acid detection that includes amplification of target sequences.

BACKGROUND OF THE INVENTION

Amplification utilizing DNA primers and a DNA polymerase is a well known technique for detecting nucleic acid target sequences. Methods for exponential amplification include the polymerase chain reaction (PCR), strand displacement amplification (SDA), nucleic acid sequence-based amplification (NASBA), transcription-mediated amplification (TMA), and rolling-circle amplification (RCA). Among numerous DNA polymerases commonly used are *Thermus aquaticus* DNA polymerase and reverse transcriptase. The design of linear DNA oligonucleotide amplification primers is generally accomplished with the acid of a computer program designed for that purpose. Among the available programs that can be utilized are PRIDE (Haas et al. 1998), OLIGO (Rychlik et al. 1989), OSP (Hilber et al. 1991), Primo (Li et al. 1997) and Primer Master (Proutski et al. 1996).

A common problem is known as "primer-dimers". Primer-dimers are false amplification products (amplicons) that are generated because two primers hybridize to each other with overhangs, thereby providing binding sites for a polymerase and initiating DNA synthesis. Primer-dimers compete with the intended amplification and generally reduce the reliability and sensitivity of an assay. Another common problem is mis-priming of a sequence in a sample that is partially complementary to the primer. This also leads to false amplicons and reduces reliability and sensitivity.

One major application for target-amplification methods is in vitro diagnostics. In diagnosing pathological conditions by nucleic acid-based techniques, a common situation is that a unique nucleic acid sequence from a pathogen is a rare component of the total nucleic acid in a clinical sample. For example, the genomic DNA of the malarial parasite is a very small fraction of the total DNA that is extracted from a patient's blood. Amplification of rare pathogenic target sequences is an effective means for detection in some cases, because primers can be designed that successfully ignore the abundant human sequences sufficiently for diagnostic purposes. However, there are many situations in which a rare target sequence is very similar to an abundant sequence, differing in some cases by only a single nucleotide. For example, certain human cancers are characterized by an alteration at just one nucleotide position in a gene (Lengauer et al., 1998). To detect these cancers at an early stage, or to detect their remnants after surgical removal of a tumor, it is necessary to detect the presence of a rare sequence that differs from an abundant sequence by only a single nucleotide. When a sequence that indicates the presence of cancer is rare, the difficulty of detecting that sequence is sometimes referred to as the "minimal residual disease problem." A similar problem arises when the emergence of a drug-resistant bacterium or virus needs to be detected as early as possible when a patient is being treated with a drug, because a number of drug-resistance genotypes are characterized by a single nucleotide substitution in a pathogenic sequence. For applications such as those described above, simple target amplification is not effective, because the primers cannot sufficiently distinguish between two sequences that differ from each other by only a single nucleotide substitution.

Two approaches have been used to address this problem. The first is to design one of the two oligonucleotide primers that are needed for amplification to bind to the target at a sequence that encompasses the site of the nucleotide substitution. If the primer is perfectly complementary to its intended target sequence, then a primer-target hybrid will form, leading to the generation of amplified copies of the target nucleic acid sequence. The hope is that if a nucleotide substitution is present, then the mismatched primer-target hybrid will not form, resulting in an inability to generate amplified copies of the nucleic acid sequence. However, this dichotomy does not work well in practice, and both the mutant and the wild-type templates result in amplification. The products of amplification of perfect and mismatched targets (the "amplicons") are indistinguishable from one another. Even if only mismatched target sequences are present in the sample, the primer will occasionally initiate DNA synthesis on the mismatched target sequence. Because the resulting product contains a perfect complement of the primer sequence, exponential amplification of this initial product occurs at a rapid rate. The second approach that is used to detect mutations in a target sequence is to utilize primers that bind outside the sequence that might contain a mutation, so that the sequence that contains the site of the mutation becomes a part of the resulting amplicons. Additional hybridization probes are then used to determine if the mutation is present within the amplicons. The proportion of amplicons containing a mutation is a measure of the relative amount or absolute amount of the mutation in the starting sample. Although this approach works well in many situations (Tyagi et al. 1996, Tyagi et al. 1998), it has a sensitivity limitation: if the mutant amplicons are less than a few percent of all the amplicons, they cannot be detected.

In order to detect mutants that are rare, that is, less abundant than the few percent of the wild-type sequence that is needed for detection by hybridization probes, an "amplification refractory mutation system" (ARMS) has been used (Newton et al., 1989; Wu et al., 1989). In this method, two amplification reactions are carried out in separate reaction tubes. The difference between the reactions is that one of the primers is slightly different in each tube. The difference between the primers is in the identity of the nucleotide at their 3' ends. The 3' nucleotide of the primer in one reaction tube is complementary to the wild-type nucleotide at the site of mutation, while the 3' nucleotide of the primer in the other reaction tube is complementary to the mutant nucleotide at the site of mutation. If the primer in the tube is perfectly complementary to its target sequence, including the nucleotide at the 3'-end of the primer, then the primer can be efficiently extended by incubation with DNA polymerase. However, if the binding of the primer in the tube to the target sequence creates a mismatched 3'-terminal nucleotide, then the primer cannot be efficiently extended by incubation with DNA polymerase. Amplification of the mismatched template is significantly delayed, i.e., the number of thermal cycles in a polymerase chain reaction (PCR) amplification that are required before the amplification product can be detected (or the amount of time it takes to generate a detectable quantity of amplification product in an isothermal amplification) is significantly greater when the 3' nucleotide of the primer is not complementary to the sequence present in the sample.

ARMS primers and conventional primers are both prone to generating false-positive signals, because they can initiate the exponential synthesis of unintended amplicons, even in absence of perfectly complementary target sequences. These "false amplicons" arise because the 3' end regions of the primers can bind to partially complementary sequences unrelated to the target that are present in samples. They also can arise from the binding of one primer molecule to another primer molecule, which results in the initiation of DNA synthesis (primer-dimers). In either case, the resulting extension products can be exponentially amplified in the normal manner, resulting in the synthesis of false amplicons. The generation of false amplicons not only makes it difficult to identify the intended amplicons, but also limits the sensitivity of assays, since false amplicons compete with the intended amplicons, and thereby reduce their abundance. For example, if a rare target sequence requires 38 cycles of PCR to be detectable above background, but a false amplicon in the reaction becomes detectable after 35 cycles, the rare target will not reach a detectable level.

The present invention markedly improves the specificity of oligonucleotide primers.

One aspect of the invention is an improvement in the sensitivity of assays that detect target nucleic acids that contain a single nucleotide substitution within a population of much more abundant wild-type nucleic acids, enabling detection at levels below a few percent.

Another aspect of the invention is a reduction in the formation of false amplification products, including primer-dimers.

Another aspect of the invention is that it enables the determination of the fraction of a nucleic acid population that is mutant and the fraction that is wild type, particularly when the fraction is very small or very large.

Another aspect of the invention is the decrease or elimination of the tendency of target amplification reactions to produce false amplicons.

Another aspect of the invention is to provide a means of labeling the amplification product with a fluorescent moiety so that the reactions can be monitored in real time without having to utilize probes or nonspecific intercalating reagents.

SUMMARY OF THE INVENTION

This invention includes oligonucleotide primers for nucleic acid amplification. When not bound to target, primers according to this invention form a particular type of hairpin structure in which the 3' terminal region of the primer is hybridized to the 5' terminal region of the primer to form a double-stranded stem. Only the central region of the primer is single stranded and available for initial hybridization to a complementary target, a process sometimes referred to as "nucleation". This invention also includes amplification methods and assays that utilize such primers, and kits for performing such assays. These methods and assays reduce false amplicon synthesis that limit existing methods and assays.

Certain primers according to this invention are useful to detect the presence of a mutant having a single nucleotide substitution in a generally wild-type population even when the amount of the mutant is below the detection limit, generally a few percent, currently achievable by the use of labeled detector probes or by the use linear primers whose 3' terminal nucleotide hybridizes at the nucleotide subject to mutation. Having the loop of primers according to this invention hybridize to a target at a sequence containing the nucleotide subject to mutation permits detection of very low levels of mutant strands.

Amplification reactions and assays according to this invention utilize at least one hairpin primer according to the invention. Exponential amplification reactions and assays (for example, the polymerase chain reaction) utilize a pair of primers, sometimes referred to as "forward" and "reverse" primers, one of which is complementary to a nucleic acid strand and the other of which is complementary to the complement of that strand. Where a pair of amplification primers is used, either one or both are hairpin primers according to this invention.

Assays according to this invention may utilize any detection method for detecting amplicons. Such methods include gel electrophoresis, intercalating dyes, minor groove binding dyes, fluorescence polarization, mass spectrometry and labeled detection probes. Detection may be end point, that is, carried out when amplification is completed, or real time, that is, carried out during the amplification process. Real-time probe-based detection methods include 5' nuclease assays (Gelfand et al., 1996; Livak et al., 1996) and molecular beacon assays (Tyagi et al., 1996; Tyagi et al., 1997; Tyagi et al., 1998). Alternatively, primers according to this invention can be labeled with interactive fluorescent label pairs such as two fluorophores or a fluorophore and a non-fluorescent quencher, such that a change in fluorescence signal indicates the presence of primers that have been extended and, thus, the presence of a target for the primers in a sample. Interaction between labels may be by fluorescence resonance energy transfer (FRET), by touching, or both. Assays utilizing labeled primers according to this invention can be real-time assays as well as end-point assays.

Kits according to this invention include amplification reagents, generally at least amplification buffer and dNTPs, and normally DNA polymerase, and at least one primer according to this invention. Kits may include additional reagents, for example detection reagents, and may include instructions for performing an assay.

BRIEF DESCRIPTION OF THE DRAWINGS

FIG. 5 shows the nucleotide sequence (SEQ ID NO:1) and the mode of attachment of the fluorophore and the quencher moieties in a labeled primer according to this invention.

FIG. 6 shows the change in the fluorescence intensity of polymerase chain reactions that utilize labeled primers according to this invention as a function of the number of thermal cycles completed.

DETAILED DESCRIPTION OF THE INVENTION

Figure 1:
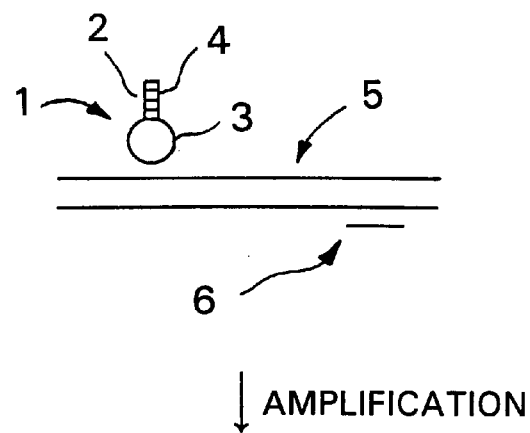
FIG. 1 is a schematic representation of the manner in which hairpin primers according to the invention are used to detect a single nucleotide substitution.

An important aspect of this invention is target-amplification methods and assays that are less prone to generating false amplicons and that are more sensitive than amplification methods and assays currently in use involving amplification of rare sequences, including the detection of rare mutant sequences within a population of wild-type sequences, or vice versa. Assays based on this invention use primers that can exist as hairpins comprising a single-stranded "loop" and a double-stranded "stem". With reference to FIG. 1, these primers 1 consist of three parts, a 5'-arm sequence 2, a central loop sequence 3, and a 3'-arm sequence 4 that is complementary to 5'-arm sequence 2. The loop 3 and the 3' arm 4 of the hairpin 1 are complementary to one strand of target 5, whereas the 5' arm 2 is designed to convert the primer into a hairpin-shaped molecule. Thus, primers according to this invention have both loops and 3' arms that are complementary to the target and a 5' arm that competes with the target for hybridization to the 3' arm. When the sequence in the loop 3 binds to its complement in the target 5, the stem of the hairpin-shaped primer 1 unravels and the 3' arm 4 anneals to the target. This creates the substrate for enzymatic extension of primer 1. Target 5 may be a single strand, or it may be double-stranded. In either case second primer 6, which may be a conventional linear primer, permits exponential amplification to produce double-stranded amplicon 7. Primers according to this invention have stems that do not unravel, or dissociate, unless both the loop and the 3' arm are complementary to the target. If a primer according to this invention is tested against a model non-target of the length of the loop and perfectly complementary to the loop the stem does not dissociate.

There are special cases in which at least a portion of 5' arm is at least partially complementary to the intended target. Following the design criteria discussed below, one may design a primer which has one or a few 3'-terminal nucleotides of the 5' arm complementary to the target. Example 4 below illustrates this situation. Instances in which the entire 5' arm will be complementary to a target will be rare.

Because the 3' portion of the primer is in a double-stranded state, the generation of false amplicons by primer-dimer formation or mis-priming of 3' ends is prohibited to a very large extent. If the sample contains a nucleic acid differing from target 5 by a nucleotide that is not complementary to the sequence in loop 3, the loop cannot bind to that nucleic acid and 3' arm 4 cannot anneal to the nucleic acid and initiate DNA synthesis. Consequently, the presence of target molecules (for example, either wild-type or mutant DNA template molecules, or wild-type or mutant RNA template molecules) in the sample results in amplicon synthesis, whereas the presence of molecules differing from the target sequence by as little as a single nucleotide substitution either does not result in amplicon synthesis, or if the primer happens on very rare occasions to bind to the mismatched template and initiate amplicon synthesis, the synthesis of the amplicons will be significantly delayed.

Referring to FIG. 1, it will be seen that in the embodiment depicted there, the terminal nucleotides of the primer are complementary and form part of stem. We refer to them as "arms". This is also true for the embodiment shown in FIG. 5. This is our preferred construction utilized in the several examples described below. However, it is within the scope of the invention that non-complementary nucleotides be included within the stem, which will reduce the strength of the stem, or included as non-complementary terminal nucleotides or the stem, for example, a single-stranded overhang. The latter presents a danger of false priming, so any overhang must be incapable of nucleation with other nucleic acid sequences so as to provide a starting point for branch migration. In primers according to this invention nucleation is by annealing of the loop sequence to the target. It will be understood that as used in this application and the appended claims "stem" and "complementary 3' and 5' arm sequences" are sufficiently broad to encompass the above variants.

It will be appreciated that, even when the 5' arm is completely non-complementary to the intended target, amplicons synthesized by copying oligonucleotides containing a primer will contain complete complements of the primer. This may reduce the discriminatory effectiveness, including the suppression of false amplicons, achieved in the first round of synthesis. To preserve to initial effect throughout amplification, certain preferred embodiments of primers according to this invention include a "terminator nucleotide" inserted between the loop and the 5' arm. As used herein, "terminator nucleotide" is a nucleotide that stops extension by a polymerase during DNA synthesis. The terminator nucleotide may be, for example, 4-methylindole β-deoxynucleoside (Moran et al., 1996). Insertion of a terminator nucleotide between the 5' arm and the loop prevents copying of the 5' arm.

Hairpin primers of the present invention can contain deoxyribonucleotides, ribonucleotides, peptide nucleic acids (PNA), other modified nucleotides, or combinations of these. Modified nucleotides may include, for example, 2'-O-methylribonucleotides or nitropyrole-based nucleotides. Modified internucleotide linkages may also be included, for example phosphorothioates. Using modified nucleotides in the 5' arm provides a way to adjust the strength of the stem. Other advantages of using such modifications for a particular application will be apparent to persons familiar with the art. In particular, hairpin primers according to this invention that are constructed from modified nucleotides may form stronger hybrids than if the primers were constructed from deoxyribonucleotides, thus enabling structured target sequences (such as those that occur in messenger RNAs) to be more easily accessed.

Certain embodiments of primers according to this invention are highly discriminatory against single nucleotide substitutions. In these embodiments the loop is complementary to the target region containing the target nucleotide subject to substitution. We place that nucleotide near the center of the loop. In addition we attempt to make the loop as short as possible, that is, from five to nine nucleotides long, to maximize the impact of a single mismatch.

Hairpin primers of the present invention permit monitoring of amplification reactions by fluorescence. They can be labeled with interactive fluorescent moieties, and with other labels, in such a manner that free primers permit the interaction of the label moieties, whereas the labels of primers that are incorporated into double-stranded amplicons do not so interact. One of the interactions that are useful in detection is fluorescence energy transfer, which causes the fluorescence of free primers to be quenched and the fluorescence of those that are incorporated into amplicons not to be quenched. As a result, the course of the amplification reactions can be monitored by measuring the fluorescence. Particularly useful is the interaction of quenching by touching, wherein a non-fluorescent quenching molecule such as DABCYL, DABMI, DABSYL or Methyl Red is used to prevent a fluorophore from fluorescing, rendering free-floating primers dark. Because (a) hairpin primers according to this invention are so specific that they are extremely unlikely to generate false amplicons, and (b) their particular hairpin shape markedly reduces the probability that they will interact with each other to form primer-dimers, the generation of a fluorescent signal in a reaction that utilizes hairpin primers according to this invention is an excellent indication that the intended amplicons have been synthesized. Furthermore, the generation of a fluorescent signal during real-time detection of the amplification products allows accurate quantitation of the initial number of target sequences in a sample. This represents an improvement over the current art. In the current art, either hybridization probes have to be used to monitor the amplification reactions, or when other methods of amplicon labeling are used, these methods are not sufficiently specific to discriminate false amplicons from the intended amplicons (Nazarenko et al., 1997; Wittwer et al., 1997).

The advantages of using hairpin primers according to this invention are unexpected. It has been a common belief that the presence of a hairpin in the priming region of a primer, deleteriously diminishes the ability of the primer to prime. Examples of such teachings can be found in computer programs that are used to design primers for polymerase chain reactions, where the algorithms reject putative primer sequences that possess self-complementary (hairpin-forming) sequences (for example, Haas et al., 1998; and Rychlik et al., 1989).

Hairpin primers of the present invention can be used to solve the problem of false amplicon synthesis in amplification reactions. Conventional primers, that is, primers whose target-complementary regions are linear, are prone to producing false amplicons because their 3' ends can bind to partially complementary sequences in either unrelated DNA or in other primers, where they initiate DNA synthesis, generating unintended templates for DNA polymerase. These templates are then amplified normally, resulting in false-positive signals. However, the sequence at the 3' end of a hairpin primer according to this invention is hybridized to the sequence at the 5' end, and thus almost never binds to a target sequence unless the loop sequence first anneals to the target sequence. The hybrid formed by the binding of the loop sequence to a portion of the target sequence then lengthens by branch migration, resulting in the binding of the 3'-arm sequence to the remainder of the target sequence. This process can not occur at all or only very rarely unless the target sequence is perfectly complementary to the loop sequence. Partially complementary sequences almost never take part in this chain of events, and priming does not occur. Therefore, except on very rare occasions, priming occurs only at perfectly complementary sites on target strands.

Hairpin primers of this invention are useful in a number of nucleic acid amplification processes that employ primers, including polymerase chain reactions (PCR), strand displacement amplification (SDA), nucleic acid sequence-based amplification (NASBA), transcription-mediated amplification (TMA), and rolling-circle amplification (RCA). The high specificity and consequent low mispriming significantly and detectably delays signal from sequences other than perfectly complementary targets. In thermal cycling amplifications, this delay is manifested in a later threshold cycle: in isothermal amplifications, in a later time for detectable signal to arise.

Nucleic acid amplification assays that utilize hairpin primers of the present invention can be designed so that the amplicons are detected by conventional methods at the end of the reaction, such as by polyacrylamide gel electrophoresis, or the products can be detected in real time during amplification using conventional detection methods. A variety of real-time detection methods, including the use of intercalating dyes and probe-based methods, can be employed (reviewed by Zubritsky, 1999), or the fluorescence of labeled hairpin primers themselves can be utilized, as described in Example 3 below.

In order to determine the fraction of mutant and wild-type sequences in a sample that are mutant, a portion of the DNA in the sample is amplified in one reaction using a wild-type-specific primer according to this invention, and a second portion of the DNA in the sample is amplified in a second reaction using a mutant-specific primer according to this invention. If amplification includes thermal cycling, the difference in the threshold cycles of the two reactions indicates the relative proportion of the mutant and the wild-type sequences in the original sample. The larger the difference, the smaller is the fraction of mutants. If amplification is isothermal, the difference in the time required for detectable signal to arise indicates the relative proportion.

Hairpin primers according to this invention can be prepared by first designing the priming sequence, the portion complementary to the intended target, that is, loop 3 and 3' arm 4 (FIG. 1), in the conventional manner. For this purpose numerous design programs are available and have been reported in the literature. See, for example, Haas et al. (1998), Rychlik et al. (1989), Hillier et al. (1991), Li et al. (1997) and Proutski et al. (1996). Generally, these programs provide a primer sequence 15–20 nucleotides long, slightly longer on occasion. Next, 5' arm 2 (FIG. 1) is designed as an oligonucleotide sequence complementary to 3' arm 4 (FIG. 1) so as to leave 5–9 nucleotides for the loop 3 (5 nucleotides for short priming sequences and 9 nucleotides for priming sequence of 19 or more nucleotides). However, if discrimination against single nucleote changes is not required, the length of the loop can be increased by several nucleotides (see Example 4), the primer with a loop thirteen nucleotides long.

In designing primers according to this invention that can initiate DNA synthesis from a perfectly complementary DNA sequence but not from a sequence that contains a single nucleotide substitution, it is necessary to maximize the specificity of the primer. Generally, the smaller the primer the more specific priming is. However, primers that are smaller than a certain length will not bind to the complementary sequence, and thus will not be able to prime DNA synthesis. Hairpin primers of the present invention achieve high specificity by virtue of their stem. The sequence of the 3' arm of the hairpin stem and the sequence of the hairpin loop are complementary to the intended (perfectly complementary) target sequence, whereas the 5'-arm sequence of the hairpin stem does not bind to the intended target sequence. However, amplicons that are generated by copying template molecules that are extension products of hairpin primers do contain a perfect complement of the entire hairpin primer sequence, and thus the 5'-arm sequence of the hairpin primer, as well as the loop sequence and 3'-arm sequence, will bind to these amplicons in subsequent rounds of amplification. The early priming events are therefore critical in determining the specificity of amplification. The longer (or stronger) the stem of the hairpin primer is, the more specific its annealing with the template will be, and therefore the more specific the priming reaction will be. However, making the stem longer also increases the total length of the primer, which makes the primer less specific. The independent optimization of each of these two design criteria would have an opposite effect on the length of the stem. There is thus an optimal length for the stem at which maximum discrimination can be achieved. Since the stem sequence is determined by the sequence of the target around the site of mutation, the optimal length will depend on the identity of the target sequence. The optimum length of the stem usually lies between 5 to 12 deoxyribonucleotides, which is our preferred range. The lower limit is for GC-rich sequences and the upper limit is for AT-rich sequences. DNA folding programs can be used to design the hairpin structures of the primers and to predict their stability (Serra and Turner, 1995).

The initial contact between the hairpin primer and the target sequence is made by the loop of the hairpin primer, because the 3' arm is bound to the 5' arm, and is therefore unavailable for initial hybridization to the target sequence. If the target is recognized to be perfectly complementary, the 3' arm dissociates from the 5' arm and binds to the target. However, if the target sequence is not perfectly complementary to the loop sequence, then the initial contact is short-lived and the primer dissociates from the target sequence. The capacity to discriminate between a perfectly complementary target sequence and a mismatched target sequence increases as the length of the loop is decreased. However, very short loops will be too small to anneal to the target. Loops of 5 to 9 deoxyribonucleotides are optimal.

A primer initially designed as described above can be tested in the intended assay utilizing perfectly complementary target molecules and in the intended assay utilizing molecules that differ by a single nucleotide. Such a test is described below in Example 1. The purpose of the test is to determine whether the degree of specificity required for the assay has been achieved. A primer according to this invention is at least 1000 times as efficient in priming the complementary target as it is in priming the sequence with the nucleotide mismatch, preferably 5000 times as efficient. We have made primers according to this invention that are 10,000 times as efficient without extensive optimization. If the primer as initially designed does not have sufficient specificity in the amplification method or assay being used, the strength of the stem should be increased. This can be, for example, by increasing the length of the 5' arm sequence by adding a nucleotide (which maintains the length of the priming sequence). An alternative to changing the length is to substitute modified nucleotides in the 5' arm. Another alternative, and one which is a preferred embodiment, is to add a terminator nucleotide between the loop and the 5' arm. The terminator nucleotide may be, for example, 4-methylindole β-deoxynucleoside (Moran et al., 1996). By using a terminator nucleotide, generated amplicons do not include the sequence complementary to the primer's 5' arm. This maintains the initial specificity in rounds of synthesis subsequent to the first round, or cycle, and thereby increases overall specificity. If the primer fails to result in amplification of its perfectly complementary target, the length of the loop should be increased. Persons skilled in the art will be able to readily optimize the primer in the manner described.

The temperature of the annealing stage during amplification is a critical parameter that influences the specificity of priming. In polymerase chain reactions, this temperature can be adjusted in order to maximize specificity. This adjustment cannot be made with methods of amplification that are isothermal. The higher the annealing temperature, the greater is the specificity. This is also true for hairpin primers of the present invention. The combined length of the loop sequence and the 3'-arm sequence is chosen in such a way that the initial probe-target hybrid that is formed by the annealing of the hairpin primer to a target sequence that is present in the sample will dissociate at a temperature that is slightly above the annealing temperature of the amplification reaction. The precise annealing temperature that provides maximum discrimination can be found empirically by either systematically changing the annealing temperature and determining the degree of discrimination, or by carrying out these measurements with a gradient thermal cycler that can employ a range of temperatures for the annealing stage.

Primers of the present invention can be labeled with interactive label moieties so that their incorporation into the products of amplification can be monitored by fluorescence. The fluorescence of primers that are incorporated into amplicons is very different from those that are not incorporated. This permits identification of the products of amplification without any further analysis. Furthermore, the use of interactive label moieties allows accurate quantification of the initial number of target molecules by performing real-time detection of the amplicons as they are synthesized.

We have described optimal methods of selecting and attaching interactive fluorophores and quenchers (as well as other label moieties) to hairpin-shaped probes called "molecular beacons" (Tyagi and Kramer, 1996; Tyagi et al., 1997; Tyagi et al., 1998). In order to obtain higher signal-to-background ratios in assays that use molecular beacons, it is desirable to have the fluorophore and the quencher be very close to each other in the hairpin state of these probes and far from each other in their target-bound state. A similar mode of attachment of the two labels is ideal for hairpin primers according to this invention. However, in molecular beacons the quencher moiety DABCYL is usually attached to the 3'-hydroxyl group, which serves to block extension of the probe at its 3' end when DNA polymerase is present. However, in a hairpin primer (whose purpose is to initiate the synthesis of a copy of the template strand) an unblocked 3'-hydroxyl group is required for extension to occur. This precludes the attachment of a label to the 3'-hydroxyl position. We have explored other ways of attaching the labels. In a first method, the fluorophore is attached to the 5' end of the 5' arm of the primer, as is the case in molecular beacons; however, the quencher is attached to an internal location within the 3' arm. The location of the quencher within the arm that brings the fluorophore and the quencher close to each other is about 4 to 6 nucleotides away from the 3' end. In a preferred embodiment, the quencher is attached to a thymidine nucleotide at one of these positions (if the sequence allows it). The attachment is accomplished by using a thymidine derivative that possesses a 6-carbon spacer emanating from the thymidine ring and which terminates in a primary amino group. The quencher can be conjugated to this primary amino group, using methods described by Tyagi and Kramer (1996). Alternatively, a thymidine phosphoramidite that contains the spacer and the quencher can be used during automated DNA synthesis, obviating the need for post-synthetic steps. Example 3 describes one such primer. In a second method thymidine residue that bears the quencher can also be placed at the 3' end of the primer. The resulting molecule serves as a good primer because the 3'-hydroxyl moiety is available for extension and is quenched very well (the two label moieties are close to each other and they are free to interact with each other).

These primers can be labeled with a variety of fluorophores that fluoresce in different color ranges. A number of these differently colored hairpin primers can be used in the same reaction mixture, so that copies of different target sequences can be generated simultaneously, and each type of amplicon will fluoresce in its own characteristic color (determined by the identity of the fluorophore linked to its hairpin primer. Methods described by Tyagi, et al. (1998) can be used to accomplish the labeling and appropriate quenching of the fluorophores in these primers.

EXAMPLE 1

We designed a target-amplification assay for the detection of a single nucleotide substitution, a point mutation, in the gene for human methylenetetrahydrofolate reductase, whose presence within the gene increases the risk of cardiovascular disease (the mutation is called the "C677T mutation"). We selected the polymerase chain reaction (PCR) as the amplification process. A pair of forward hairpin primers was designed to recognize the sequence of the gene within which the mutation is located. Each of these primers consisted of three parts, a 5' arm, a central loop, and a 3' arm that is complementary to the 5' arm. The sequence formed by the 3' arm and the loop was complementary to the target sequence (which encompassed the site of the C677T mutation). The two hairpin primers were identical, except for one nucleotide in the loop. One of the primers was complementary to the wild-type target sequence and the other primer was complementary to the mutant target sequence. The sequence of the wild-type-specific primer was 5'-GATGAAAGGAGCCGATTTCATC-3' (SEQ ID NO:1) and the sequence of the mutant-specific primer was 5'-GATGAAAGGAGTCGATTTCATC-3'(SEQ ID NO:2), where underlines identify the arm sequences and a bold letter in each sequence identifies the nucleotide that is perfectly complementary to one of the variant nucleotides that can occur at the site of the C677T mutation. Each of these forward primers was used in a separate reaction in combination with a common reverse primer (a conventional linear primer) to amplify a small segment of the methylenetetrahydrofolate reductase gene. One of the two polymerase chain reactions was initiated with wild-type template, and the other polymerase chain reaction was initiated with mutant template, and the progress of each reaction was monitored in real-time with the aid of an intercalating dye, SYBR Green, to render the resulting amplicons fluorescent. Also, as a control, we used a conventional forward primer in place of the hairpin primer, whose target sequence was outside the site of the C677T mutation. This "neutral" forward primer enabled the synthesis of wild-type amplicons and mutant amplicons at the same rate.

The conditions of the assays were such that each 50-$\mu$l reaction contained 20,000 template DNA molecules (either mutant or wild-type), 0.1 $\mu$M of the wild-type-specific forward hairpin primer (or 0.5 $\mu$M of the conventional forward primer whose target sequence was outside of the site of the C677T mutation), 0.5 $\mu$M of conventional reverse primer, 0.25 mM dATP, 0.25 mM dCTP, 0.25 mM dGTP, 0.50 mM dUTP, 2.5 units of AmpliTaq Gold DNA polymerase (Perkin-Elmer), 50 mM KCl, 3.5 mM $MgCl_2$, 1× SYBR Green (Molecular Probes, Inc.), and 10 mM Tris-HCl (pH 8.3). Forty cycles of amplification (94° C. denaturation for 30 sec, 55° C. annealing for 60 sec, and 72° C. polymerization for 30 sec) were carried out in an Applied Biosystems 7700 Prism spectrofluorometric thermal cycler in sealed tubes. Green fluorescence was monitored in real time during the annealing stage of each cycle. Fluorescence as a function of PCR cycle number for each amplification is shown in FIG. 2., where curve 21 is from the reaction containing the linear forward primer and 20,000 molecules of wild-type template; curve 22, the linear forward primer and 20,000 molecules of the mutant template; curve 23, the wild-type-specific hairpin primer and 20,000 molecules of wild-type template; and curve 24, the wild-type-specific hairpin primer and 20,000 molecules of the mutant template.

Figure 2:
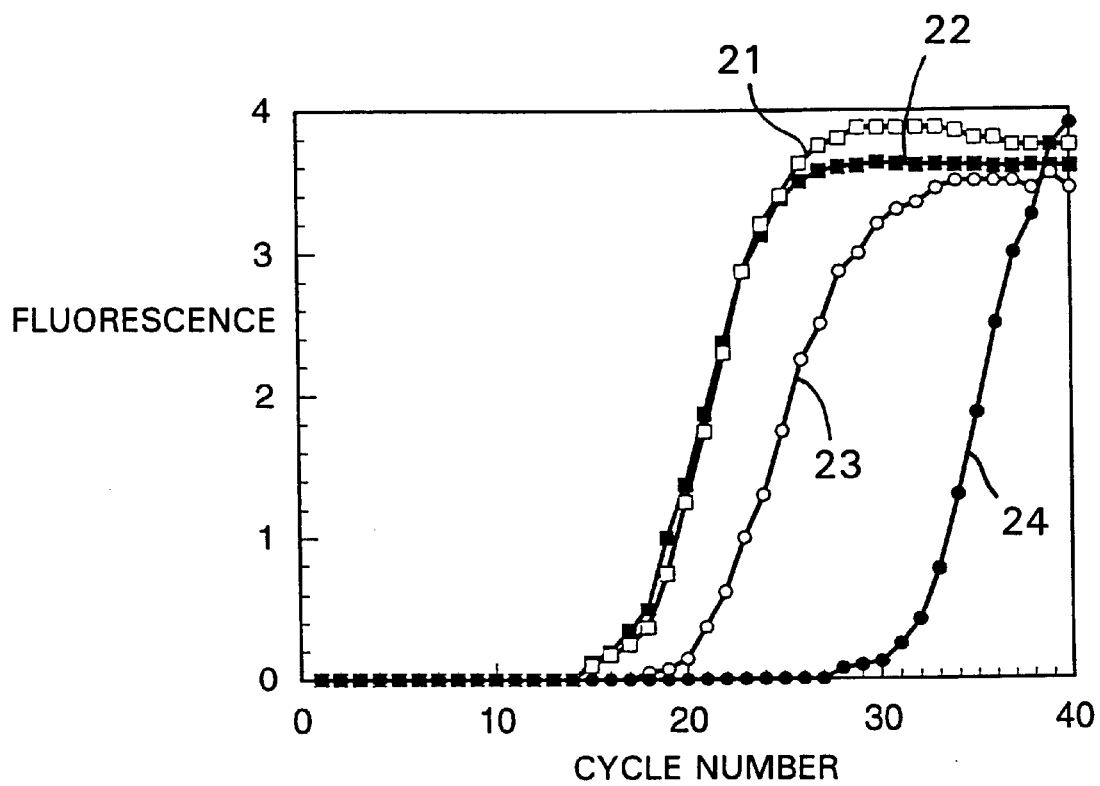
FIG. 2 shows the changes in fluorescence intensity of polymerase chain reactions (PCR's) according to this invention that detect a single nucleotide substitution as a function of the number of thermal cycles completed.

The increase in the fluorescence of each of the four reactions that were performed is shown in FIG. 2. The "threshold cycle," which is the thermal cycle at which each reaction became positive (i.e., the thermal cycle at which the intensity of the fluorescence signal became 10 times as strong as the standard deviation of the florescence background), is indicative of the number of template molecules that were initially present in the reaction. When the conventional, or neutral, primer was used as the forward primer (in place of one of the hairpin primers), the same threshold cycle (thermal cycle 16) was observed irrespective of whether 20,000 molecules of the wild-type template was initially present or whether 20,000 molecules of the mutant template was initially present, indicating that the reactions were initiated with same number of template molecules (curves 21, 22). However, when the wild-type-specific hairpin primer was used, the reaction initiated with 20,000 molecules of wild-type template became positive after 20 cycles (curve 23), whereas the reaction initiated with 20,000 molecules of mutant template only became positive after 31 cycles (curve 24). Since the number of amplicons doubles in every thermal cycle, the 11-cycle difference in the threshold cycle observed for each reaction indicates that the "delayed" reaction was initiated with ½,000th as many template molecules as was the "faster" reaction. However, these two reactions were actually initiated with the same number of template molecules. The apparent delay indicates that the wild-type-specific primer was ½,000th as efficient in priming amplicon synthesis when mutant template was used to initiate the reaction than it was when wild-type template was used to initiate the reaction. These results imply that assays containing hairpin primers can detect mutant target molecules that are ½,000th as abundant as wild-type target molecules. In other experiments that utilized the same templates and the same hairpin primers (and also in experiments that utilized different templates and appropriate wild-type-specific and mutant-specific hairpin primers) we have observed threshold cycle differences as great as 14 thermal cycles. These results demonstrate that assays containing hairpin primers can be used to detect mutant target molecules that are ¹⁄₁₀,000th as abundant as wild-type target molecules.

EXAMPLE 2

Figure 3:
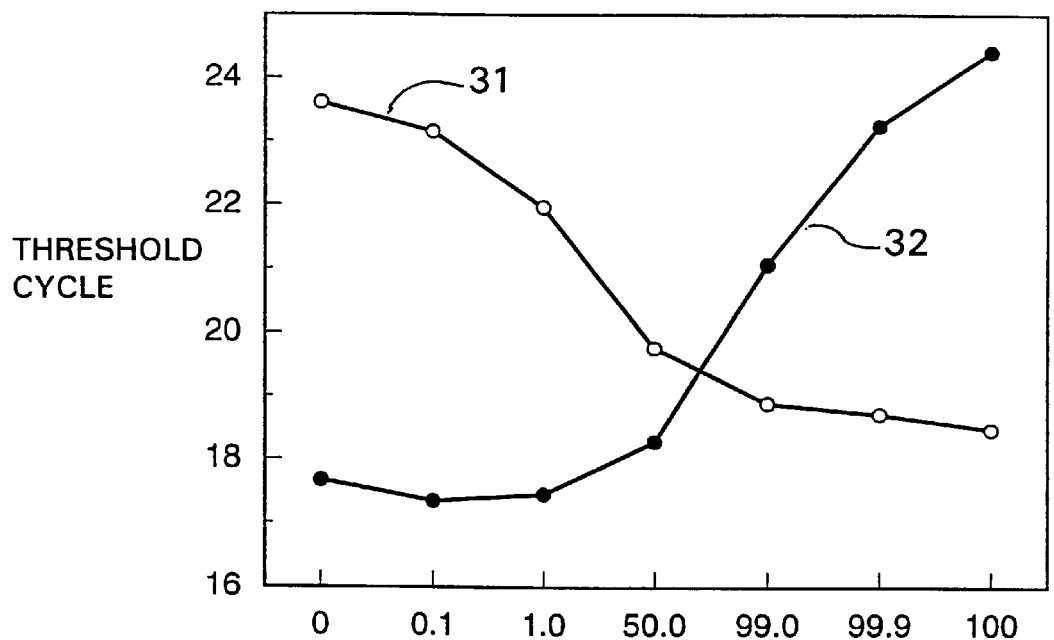
FIG. 3 shows how the PCR threshold cycle changes, when primers according to this invention are used, either mutant-specific primers or wild-type-specific primers, as a function of the proportion of mutant targets that are present in a mixture of molecules that contains both mutant and wild-type sequences (where the mutant sequence differs from the wild-type sequence by only a single nucleotide substitution).
Figure 4:
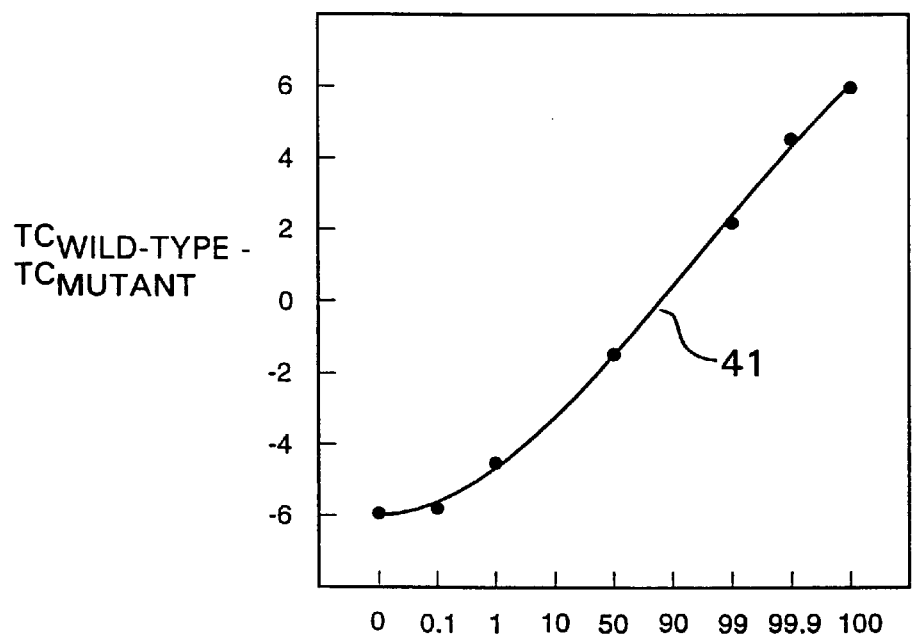
FIG. 4 shows a standard curve that enables the threshold cycles measured in two different polymerase chain reactions (one reaction containing a wild-type-specific primer according to this invention and the other reaction containing a mutant-specific primer according to this invention) to be used to measure the relative abundance of mutant targets in a population of molecules that contains both mutant and wild-type sequences (where the mutant sequence differs from the wild-type sequence by only a single nucleotide substitution).

In order to demonstrate the utility of hairpin primers according to this invention for the detection of rare mutant targets in a population containing abundant wild-type targets, we performed a series of polymerase chain reactions that were initiated with mixtures of mutant templates and wild-type templates. The proportion of mutant templates in these mixtures was varied from 0, 0.1, 1.0, 50.0, 99.0, 99.9, to 100 percent, with the total concentration of template DNA always being the same (20,000 molecules). Each of these mixtures was amplified using a wild-type-specific hairpin primer in one reaction and the corresponding mutant-specific hairpin primer in a second reaction. These primers differed by a single nucleotide. The conditions of the reactions were the same as described for Example 1. The threshold cycles that were obtained with each template mixture are plotted in FIG. 3, in which curve 32 shows the results obtained for reactions that contained wild-type-specific primer, and curve 31 shows the results obtained for reactions that contained mutant-specific primer. The results show that pure wild-type templates give a low threshold cycle with wild-type-specific primers and a high threshold cycle with mutant-specific primers. The reverse is true for pure mutant templates. While the difference in the threshold cycles that are obtained is maximum for the pure templates, the difference decreases as the proportion of one type of template is raised and the proportion of the other type of template is decreased. As little as 0.1 percent of the mutant template in a population that contained 99.9 percent the wild-type template is distinguishable from a pure wild-type template. FIG. 4 shows how the data obtained in the experiment shown in FIG. 3 can be used to establish a standard curve in which the difference between the threshold cycles (TC) measured in two different amplification reactions, here polymerase chain reactions, carried out with each sample (one reaction containing the wild-type-specific hairpin primer and the other reaction containing the mutant-specific hairpin primer) is plotted against the fraction of mutant targets in the population of mutant and wild-type targets that are present in the sample. The difference is obtained by subtracting the threshold cycle obtained from the reaction containing the mutant-specific hairpin primer from the threshold cycle obtained from the reaction containing the wild-type-specific hairpin primer. This curve 41, which was obtained using known samples, can be utilized as a standard to determine the proportion of mutant templates that are present in an unknown sample. These results show that hairpin primers of the present invention are suitable for diagnosing minimal residual disease that originates from single nucleotide substitutions.

EXAMPLE 3

In order to demonstrate that hairpin primers according to this invention can be labeled in such a way that their fluorescence increases upon their incorporation into amplicons, we synthesized a hairpin primer 51 whose sequence is shown in FIG. 5. The primer had a loop sequence eight nucleotides long, a stem seven nucleotides long, resulting in a target-complementary sequence 15 nucleotides long. A DABCYL quencher moiety 52 was covalently linked to the fifth nucleotide from the 3' end of the oligonucleotide (which was a thymidine nucleotide) via a hexalkyl spacer 53 and a fluorescein moiety 54 was covalently linked to the 5' end of the oligonucleotide, also via a hexalkyl spacer 55. The methods described by Tyagi and Kramer (1996) were utilized for the construction of this primer. We found that the fluorescence of the fluorophore 54 in this primer was quenched when the primer was incubated in the absence of target nucleic acids. When this primer was incubated in the presence of perfectly complementary targets, its fluorescence increased substantially. This primer was utilized in two polymerase chain reactions carried out under the same conditions described for Example 1, with the exception that the intercalating fluorescent dye, SYBR Green, was omitted. The first reaction was initiated with 20,000 template molecules that contained a target sequence that was perfectly complementary to the loop sequence and 3' arm sequence of the hairpin primer, whereas the second reaction contained no template DNA. The intensity of fluorescein fluorescence was monitored in real-time during each annealing stage of the polymerase chain reaction, and the results are plotted for both reactions as a function of the number of thermal cycles completed in FIG. 6. The results show that the fluorescence of the reaction mixture initiated with template DNA, curve 61, increases dramatically when the polymerase chain reaction enters the linear phase. However, the fluorescence of the reaction that did not contain any template DNA, curve 62, remained low throughout the course of the polymerase chain reaction. A comparison of the fluorescence intensity of the two reaction mixtures at the end of the amplification process indicates that their fluorescence is so different that the reaction initiated in the absence of template DNA could easily be distinguished from the reaction initiated with template DNA simply by illuminating the reaction tubes with an ultraviolet lamp. We also synthesized hairpin primers according to this invention that utilized a different labeling scheme from the one mentioned above, and we tested the resulting labeled hairpin primers. In this alternative labeling scheme, the 3' end of the primer was a thymidine nucleotide that was covalently linked to a fluorescein moiety via a hexalkyl spacer that was linked to the nucleotide, rather than being linked to the 3'-hydroxyl group of the deoxyribose moiety. This primer contained a 5'-DABCYL moiety. The primer was well quenched and its fluorescence was restored when it was incorporated into amplicons. Despite the linkage of the fluorescein moiety to the 3' nucleotide, this primer was extended normally by incubation with DNA polymerase in an amplification reaction.

EXAMPLE 4

In order to demonstrate that hairpin primers of the present invention solve the problem of false amplicon synthesis during amplification reactions, we utilized a pair of conventional linear primers that normally produce false amplicons when the amplification reactions that employ them are initiated without any template DNA. Using the sequence of these primers, we designed and constructed hairpin primers according to this invention for the same target sequences as the conventional primers were designed to bind to. We then demonstrated that when the corresponding hairpin primers are used in place of the conventional primers in a polymerase chain reaction, they generate the expected amplicons in reactions initiated with target template DNA, but (unlike reactions containing conventional primers) they do not generate false amplicons in reactions initiated without template DNA. The sequences of the first conventional primer was 5'-GGCCGGTGGTCGCCGCG-3' (SEQ ID NO:3) and the sequence of the second conventional primer was 5'-ACGTGACAGACCGCCGGGC-3' (SEQ ID NO:4). The sequence of the first corresponding hairpin primer was 5'-CGCGGCCGGTGGTCGCCGCG-3' (SEQ ID NO:5) and the sequence of the second corresponding hairpin primer was 5'-GCCCGGACGTGACAGACCGCCGGGC-3' (SEQ ID NO:6), where underlines identify the arms of the hairpins. These primers were designed to amplify a region of the RNA polymerase gene of *Mycobacterium tuberculosis*.

Figure 7:
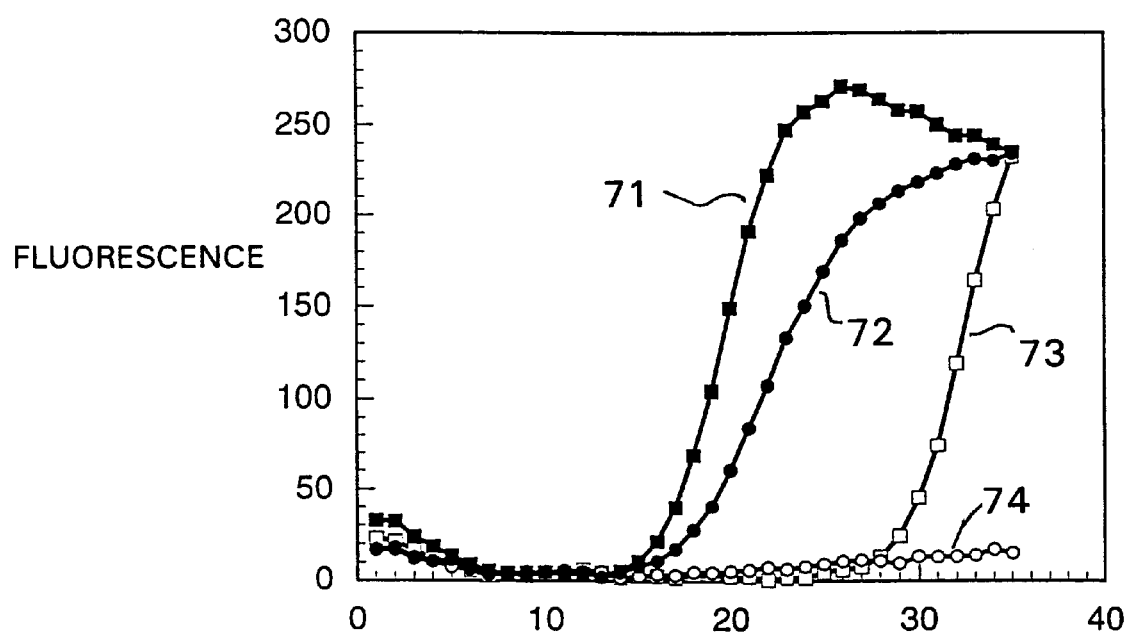
FIG. 7 shows changes in the fluorescence intensity of polymerase chain reactions that utilize primers according to this invention as a function of the number of thermal cycles completed.

The design of the first and second hairpin primers is illustrative of two design points. For the first hairpin primer we noted that a loop eight nucleotides long and a stem six nucleotides long could be obtained by adding only three nucleotides to the 5' terminus of the first conventional primer. That was possible in this particular instance, because of fortuitous complementarily. Note that three nucleotides in the 5' arm are there nucleotides at the 5' end of the first conventional primer. For the second hairpin primer the 5' arm includes six added nucleotides. However, in this instance note that the loop, thirteen nucleotides long, is outside the preferred range of 5–12 nucleotides. In this instance we were not attempting to discriminate against a single nucleotide substitution. Four polymerase chain reactions were performed, two containing the conventional primers, and two containing the hairpin primers. One of the reactions in each pair was initiated with target template DNA, whereas the other reaction in the pair did not contain any template DNA. The progress of these reactions was monitored using the fluorescent intercalating dye, SYBR Green, to label any amplicons that were generated in the course of the amplification reactions. The changes in fluorescence intensity that were observed during the course of the amplification reactions is shown in FIG. 7. The results show that the reaction that contained the first and second conventional primers and 20,000 template molecules, curve 71, became positive after 16 thermal cycles had been completed, and the reaction that contained those conventional primers and no template DNA, curve 73, became positive after 29 thermal cycles had been completed, indicating that false amplicons were generated in the course of the reaction. A subsequent analysis of these amplicons by polyacrylamide gel electrophoresis showed that legitimate amplicons were produced in the first reaction, whereas false amplicons of an unexpected size were produced in the second reaction. We believe the false amplicons were primer-dimers. However, when the first and second hairpin primers were used in place of the conventional primers, the reaction initiated with 20,000 target template molecules, curve 72, became positive after 17 thermal cycles had been completed, but the reaction that did not contain any template molecules, curve 74, never became positive. Subsequent analysis of the amplicons by polyacrylamide gel electrophoresis confirmed that the first reaction generated the expected amplicons, and the second reaction did not generate any amplicons. These results confirm that hairpin primers of the present invention are useful in solving the problem of false amplicon synthesis during amplification reactions. The reason that hairpin primers suppress the synthesis of false amplicons is that only the sequence in the loop is available for initiating the primer-template hybrid, and the presence of a hybridization sequence in a hairpin loop renders the interaction between the primer and the target nucleic acid much more specific than the interaction that occurs when a conventional linear primer hybridizes to a target nucleic acid. Moreover, the structure of hairpin primers is such that the sequences that are present in the arms of the primer do not participate in the initial hybridization of the primer to the target nucleic acid. Consequently, the binding of one primer to another during an amplification reaction (which can create undesirable amplifiable primer-dimers when conventional linear primers are used) is much less likely to occur when hairpin primers are used.

REFERENCES

Gelfand et al. (1996) U.S. Pat. No. 5,487,972.

Haas, S., Vingron, M., Poustka, A., and Wiemann, S. (1998) Primer design for large scale sequencing. Nucleic Acids Res. 26, 3006–3012.

Lengauer, C., Kinzler, K. W., and Vogelstein, B. (1998) Genetic instabilities in human cancers. Nature 396, 643–649.

Livak et al., (1996) U.S. Pat. No. 5,538,848.

Monia, B. P., Johnston, J. F., Ecker, D. J., Zounes, M. A., Lima, W. F., and Freier, S. M. (1992) Selective inhibition of mutant Ha-ras mRNA expression by antisense oligonucleotides. J. Biol. Chem. 267, 19954–19962.

Moran et al., (1996) Nucleic Acids Res. 24, 2044–2052.

Nazarenko, I. A., Bhatnagar, S. K., and Hohman, R. J. (1997) A closed tube format for amplification and detection of DNA based on energy transfer. Nucleic Acids Res. 25, 2516–2521.

Newton, C. R., Graham, A., Heptinstall, L. E., Powell, S. J., Summers, C., Kalsheker, N., Smith, J. C., and Markham, A. F. (1989) Analysis of any point mutation in DNA. The amplification refractory mutation system (ARMS). Nucleic Acids Res. 17, 2503–2516.

Serra, M. J., and Turner, D. H. (1995) Predicting thermodynamic properties of RNA. Methods Enzymol. 259, 242–261.

Tyagi, S., and Kramer, F. R. (1996) Molecular beacons: probes that fluoresce upon hybridization. Nat. Biotechnol. 14, 303–308.

Tyagi et al. (1997) Published PCT patent application WO97/39008.

Tyagi, S., Bratu, D. P., and Kramer, F. R. (1998) Multi-color molecular beacons for allele discrimination. Nat. Biotechnol. 16, 49–53.

Wittwer, C. T., Herrmann, M. G., Moss, A. A., and Rasmussen, R. P. (1997) Continuous fluorescence monitoring of rapid cycle DNA amplification. Biotechniques 22, 134–138.

Wu, D. Y., Ugozzoli, L., Pal, B. K., and Wallace, R. B. (1989) Allele-specific enzymatic amplification of beta-globin genomic DNA for diagnosis of sickle cell anemia. Proc. Natl. Acad. Sci. USA 86, 2757–2560.

Zubritsky, E. (1999) Pinning down PCR. Anal. Chem. 71, 191A–195A.

We claim:

1. A process for nucleic acid amplification comprising the extension by a DNA polymerase of at least one hairpin oligonucleotide primer comprising a 3' arm sequence, a 5' arm sequence and a single-stranded loop sequence separating said arm sequences, said 3' arm sequence and said loop sequence both being perfectly complementary to a selected priming region of a target nucleic acid strand, and said arm sequences having sufficient complementarity to one another to form a double-stranded stem hybrid in the absence of the target strand, wherein said primer hybridizes to said target strand overcoming the stem hybrid, wherein said stem hybrid is sufficiently strong that hybridization of the loop sequence to a sequence of the length of the loop and perfectly complementary to the loop sequence does not cause dissociation of the stem, and wherein said 3' arm sequence contains insufficient nucleotides that are not complementary to said 5' arm sequence to nucleate hybridization of the primer to the target.

2. The process according to claim 1 wherein said nucleic acid amplification is selected from the group consisting of a polymerase chain reaction (PCR), a strand displacement reaction (SDA), a nucleic acid sequence-based amplification (NASBA), a transcription-mediated amplification(TMA), and a rolling-circle amplification (RCA).

3. The process according to claim 2 wherein said nucleic acid amplification process includes a pair of primers.

4. The process according to claim 2 wherein said at least one hairpin oligonucleotide primer includes a terminator nucleotide between the loop and the 5' arm.

5. The process according to claim 1 including real-time detection of intended amplification products utilizing separate detector probes having interactive labels, at least one of which is a fluorophore.

6. The process according to claim 1 including real-time detection, wherein said at least one primer additionally comprises interactive fluorescent label moieties attached to the 3' and 5' arm sequences, whereby incorporation of the primer into a double-stranded nucleic acid detectably alters the fluorescence emitted by said label moieties.

7. The process according to claim 6 wherein said interactive fluorescent label moieties comprise a fluorophore and a non-fluorescent quencher.

8. The process according to claim 1 wherein said loop sequence is 5 to 9 nucleotides in length and said complementary 3' and 5' arm sequences form a stem that is 5 to 12 nucleotides in length.

9. The process according to claim 8 wherein said priming region contains a single nucleotide subject to mutation and said loop sequence is complementary to the portion of said priming region containing said nucleotide.

10. The process according to claim 8 wherein said primer contains modified nucleotides, modified internucleotide linkages, or both.

11. The process according to claim 1 wherein said at least one hairpin oligonucleotide primer includes a terminator nucleotide between the loop and the 5' arm.

12. The process according to claim 1 wherein said priming region contains a single nucleotide subject to mutation and said loop sequence is complementary to the portion of said priming region containing said nucleotide.

13. The process according to claim 12 wherein said primer additionally comprises interactive fluorescent label moieties attached to the 3' and 5' arm sequences, whereby incorporation of the primer into a double-stranded nucleic acid detectably alters the fluorescence emitted by said label moieties.

14. The process according to claim 13 wherein said interactive fluorescent label moieties comprise a fluorophore and a non-fluorescent quencher.

15. The process according to claim 1 wherein said nucleic acid amplification process includes a pair of primers.

16. The process according to claim 15 wherein said pair of primers comprises at least one primer having a loop sequence 5 to 9 nucleotides in length and said complementary 3' and 5' arm sequences form a stem that is 5 to 12 nucleotides in length.

* * * * *